United States Patent [19]

Robschlager

[11] Patent Number: 4,925,995

[45] Date of Patent: May 15, 1990

[54] PROCESS FOR PREPARING LIQUID HYDROCARBONS

[75] Inventor: Karl H. Robschlager, Amsterdam, Netherlands

[73] Assignee: Shell Oil Company, Houston, Tex.

[21] Appl. No.: 311,259

[22] Filed: Feb. 16, 1989

[30] Foreign Application Priority Data

Mar. 21, 1988 [GB] United Kingdom ................ 8806675

[51] Int. Cl.$^5$ .............................................. C07C 4/00
[52] U.S. Cl. .................................. 58.5/310; 585/326; 585/329; 585/533
[58] Field of Search ............... 585/533, 254, 324, 326, 585/329; 208/49

[56] References Cited

U.S. PATENT DOCUMENTS

| | | | |
|---|---|---|---|
| 3,475,345 | 10/1969 | Benesi | 502/74 |
| 4,482,772 | 11/1984 | Tabak | 585/254 |
| 4,511,747 | 4/1985 | Wright et al. | 585/533 |
| 4,513,166 | 4/1985 | Sakurada et al. | 585/585 |
| 4,544,788 | 10/1985 | Daviduk et al. | 585/401 |
| 4,544,792 | 10/1985 | Smith et al. | 585/533 |
| 4,547,612 | 10/1985 | Tabak | 585/415 |
| 4,560,536 | 12/1985 | Tabak | 208/70 |
| 4,835,335 | 5/1989 | van der Berg et al. | 585/329 |

OTHER PUBLICATIONS

Chem. Abs., 107:137352p.
Chem. Abs., 88:136051s.

*Primary Examiner*—Anthony McFarlane
*Attorney, Agent, or Firm*—Ronald R. Reper

[57] ABSTRACT

The invention relates to a process for preparing liquid hydrocarbons (e.g., middle distillates or gasoline) comprising at least the following steps:

(i) catalytically oligomerizing an olefins-containing feed, (ii) separating effluent from step (i) into at least two fractions of which at least one (e.g., a gasoline fraction) has a boiling range above that of the feed olefins, and (iii) recycling at least part of a higher boiling fraction obtained from step (ii) to step (i).

Optionally, in a further step (iv), a higher boiling fraction is hydrocracked, e.g., to prepare additional gasoline and/or middle distillates.

6 Claims, No Drawings

PROCESS FOR PREPARING LIQUID HYDROCARBONS

BACKGROUND OF THE INVENTION

The invention relates to a process for preparing liquid hydrocarbons.

It is known to prepare liquid hydrocarbons (having a boiling point above ambient temperature at a pressure of 1 bar) from an olefins-containing feed with a solid oligomerization catalyst at oligomerization conditions, to separate the normally liquid products from unconverted feed and to recycle said feed to the oligomerization zone in order to increase the yield of liquid products.

A disadvantage of the known process is that the composition of the liquid products thus produced is more or less fixed, i.e., depending on the type of catalyst and process conditions applied the product slate comprises certain fractions of gasoline, middle distillates (comprising kerosine and naphtha) and a usually small fraction of still higher boiling compounds.

Moreover, in some cases the stability of the catalyst is not as high as would be desired for a commercial operation, probably due to the deposition of some of the highest boiling compounds on the catalyst.

An object of the invention is to provide a process which is very flexible towards the preparation of various desired liquid hydrocarbon fractions, at stable operating conditions and without loss of olefins conversion, compared with known processes.

Surprisingly, it has now been found that specific desired liquid hydrocarbon fractions can be prepared by separating effluent from an oligomerization zone into at least two fractions having different boiling ranges, and recycling at least part of a fraction having a boiling range above that of the feed olefins to the oligomerization zone.

SUMMARY OF THE INVENTION

The invention therefore relates to a process for preparing liquid hydrocarbons which comprises at least the following steps:

(i) contacting an olefins-containing feed with a solid oligomerization catalyst at oligomerization conditions, (ii) separating effluent from step (i) into at least two fractions of which at least one has a boiling range above that of the feed olefins, and (iii) recycling at least part of a higher boiling fraction obtained from step (ii) to step (i).

DESCRIPTION OF THE PREFERRED EMBODIMENTS

In step (ii) of the process, according to the invention at least part, and preferably all, of the effluent from oligomerization step (i) is separated into the desired fractions, preferably by means of distillation (which may be preceded by a flashing stage in order to remove lower boiling compounds such as unconverted feed gas from the effluent and recycling only such gas from step [ii] to step. [i]).

The hydrocarbon fraction which is to be recycled to step (i) preferably has a boiling range at an atmospheric pressure substantially above 50° C.; in particular a gasoline fraction boiling in the range from 50° C. to 150° C., or even a higher boiling fraction, e.g., from 50° C. up to 220° C., is recycled in order to attain optimum middle distillate yields.

In case it is desired to prepare mainly lubricating base oils having a viscosity index of more than 120, or even more than 150 by the process according to the invention, a hydrocarbon fraction boiling above 150° C., in particular above 200° C., obtained from step (ii) is recycled to step (i). Such a fraction includes middle distillates (i.e., kerosine and naphtha) boiling up to about 350° C., but preferably not a substantial amount of higher boiling hydrocarbons which form part of the desired product. Recycle of such middle distillates furthermore results in improved temperature control in the oligomerization zone due to the substantial heat of evaporation of middle distillates, compared with gasoline fractions.

Surprisingly, it has been found that recycling of higher boiling fractions than the olefins feed does not render it necessary to increase the catalyst bed volume in the oligomerization zone in order to maintain the olefins conversion at least at the same level as without recycle of such higher boiling fractions, i.e., the conversion does not decrease at an increasing overall space velocity, in particular when the oligomerization catalyst applied in step (i) comprises nickel on a mordenite-type of crystalline aluminium silicate as carrier. Without wishing to be bound by a particular theory to explain this surprising phenomena, it appears that it is the result of a higher reaction rate between olefin feed molecules (e.g., butenes and/or propene) and a recycle product molecule (having at least six carbon atoms, such as those present in gasoline, kerosine or naphtha) than the reaction rate between two olefin feed molecules.

Monoolefins are preferably used as feed (components). The olefins preferably have at most six carbon atoms per molecule ($C_6^-$ olefins); preferably, the olefins employed as feed for step (i) contain compounds having 3 or 4 carbon atoms, i.e., propene and in addition 1-butene, 2-butene and 2-methyl propene.

In addition, the olefins-containing feed to step (i) suitably contains (cyclic) paraffins, in particular from 1 to 50% by weight.

Furthermore, the feed may contain di-olefins and mono-olefins having more than six carbon atoms per molecule and/or aromatic compounds.

The olefins-containing feed is suitably obtained as by-product from (fluid) catalytic cracking processes, thermal cracking processes (e.g., for the preparation of ethene), coking- and/or pyrolysis processes.

Suitable feeds for the present process can also be prepared starting from synthesis gas which is first converted into methanol and subsequently into a product substantially consisting of $C_6^-$ olefins. Alternatively, the synthesis gas can be converted in the presence of a Fischer-Tropsch type of catalyst into a product which in addition to paraffinic hydrocarbons contains a considerable amount of $C_6^-$ olefins.

The solid catalyst employed in step (i) of the process according to the invention preferably comprises at least one metal (Z) selected from the group consisting of metals from Groups 1b, 2a, 2b, 3a, 4b, 5b, 6b and 8 of the Periodic Table of the Elements and a crystalline trivalent metal (Q) silicate.

Reference is made to the Periodic Table of the Elements as published in the "Handbook of Chemistry and Physics", 55th edition (1975), CRC Press, Ohio, U.S.A.

Preferably, at least part of the amount, and most preferably the total amount, of metal(s) Z has(have)

been incorporated into the catalyst by means of ion exchange. Preferably, the catalyst applied in step (i) of the process according to the invention is prepared by using a mordenite-type of carrier material, which comprises exchangeable cations such as alkali metal-, hydrogen- and/or preferably ammonium ions. The carrier material is suitably treated one or more times with a solution of at least one metal salt such as an aqueous solution of a metal nitrate or -acetate. The ion exchange treatment is suitably carried out at a temperature from 0° C. up to the boiling temperature of the solution, and preferably at a temperature from 20°-100° C.

The molar ratio Z:Q is preferably greater than 0.5. Z is preferably selected from the group consisting of the metals copper, zinc, cadmium, magnesium, calcium, strontium, barium, titanium, vanadium, chromium, manganese, iron, cobalt and nickel. A particularly preferred metal Z is nickel.

The trivalent metal Q which is present in the crystal structure of the mordenite-type of metal silicate catalyst carrier used in step (i) preferably comprises at least one metal selected from the group consisting of aluminium, iron, gallium, rhodium, chromium and scandium. Most preferably Q consists substantially of aluminium; the resulting crystalline aluminium silicate preferably comprises a major part of mordenite and most preferably consists substantially completely of mordenite.

If desired (e.g., in order to increase the crushing strength of the catalyst particles), the carrier material and/or the ready catalyst for step (i) of the present process can be combined with a binder material such as (a combination of) refractory oxides(s), clay and/or carbon. Suitable refractory oxides comprise alumina, silica, magnesia, zirconia, titania and combinations thereof.

Step (i) is preferably carried out at a temperature from 150°-330° C., a pressure from 1-100 bar and a space velocity from 0.1-10 kg olefins feed/kg catalyst hour. Most preferably, step (i) is carried out at a temperature from 180°-300° C., a pressure from 10-50 bar and a space velocity from 0.2-1.5 kg olefins feed/kg catalysthour.

In a preferred embodiment of the process according to the invention at least one of the hydrocarbon fractions obtained from step (ii) having a boiling range above that of the feed olefins is contacted in step (iv) with a hydrocracking catalyst in the presence of hydrogen at hydrocracking conditions in order to reduce the product fraction boiling above the middle distillate boiling range of 150°-350° C. and, if required to increase the amount of gasoline relative to the amount of middle distillates in the product.

Steps (i) and (iv) of the process according to the invention can be carried out in one or more fixed-, moving- and/or fluidized beds or in a slurry-type of reactor; preferably, the process is carried out in fixed beds of catalyst particles such as extrudates, pellets or spheres passing sieve openings having a width from 0.05-5 mm, and preferably from 0.1-2 mm.

Step (iv) is preferably carried out at a temperature from 200°-500° C., a pressure from 1-100 bar, a space velocity from 0.1-10 kg hydrocarbon feed/kg catalyst hour and a hydrogen/hydrocarbon feed ratio of 0.5-3.0 $Nm^3/kg$. Most preferably, step (iv) is carried out at a temperature from 250°-350° C., a total pressure from 10-50 bar, a space velocity from 0.2-5 kg hydrocarbon feed/kg catalyst.hour and a hydrogen/hydrocarbon feed ratio of 0.75-1.25 $Nm^3/kg$.

Suitable hydrocracking catalysts for use in step (iv) of the process according to the invention comprise at least one metal from Groups 5b, 6b and 8 of the Periodic Table of the Elements as referred to hereinbefore, in particular chromium, molybdenum, tungsten, iron, cobalt, nickel, platinum and/or palladium on a carrier. Suitable carrier materials include amorphous refractory oxides such as silica, alumina, zirconia, magnesia, titania and mixtures thereof, in particular silica-alumina, and crystalline metal silicates having appropriate pore sizes for the presently employed hydrocarbon feeds.

Preferably, at least part of the effluent obtained from step (iv) is separated (e.g. by means of distillation) into at least two fractions of which at least one has a boiling range above that of a gasoline fraction (having a boiling range of about 50°-150° C.). At least part of the higher boiling hydrocarbon fraction(s) is preferably recycled to at least one of the steps (i) and (iv).

In case gasoline is a preferred product of the present process, at least part of the gas-oil fraction (boiling range from about 250°-350° C.) and the fraction substantially boiling above 350° C., and optionally part of the kerosene fraction (boiling range from about 150°-250° C.) are recycled to step (i) and/or (iv) in order to maximize gasoline production. Moreover, recycling of heavy fractions (boiling higher than gasoline) to the oligomerization zone in step (i) results in increased oligomerization catalyst stability in many cases, in particular when a nickel/mordenite catalyst is applied. It appears that the presence of recycled hydrocarbons which are liquid at the prevailing conditions in step (i) is an important factor for such increased catalyst stability whereas a recycled gasoline fraction would at least partly vaporize under the prevailing conditions without removing heavy residue from the oligomerization catalyst as liquid hydrocarbons seem to effect.

Furthermore, recycling of heavy fractions obtained from step (iv), and thus indirectly obtained from step (ii) (via step [iii]), makes it possible to decrease or even altogether omit gasoline recycle from step (ii) to step (i), which results in an even higher gasoline output of the process according to the invention without loosing the beneficial effect of the presence of a recycled liquid hydrocarbon fraction in the oligomerization zone.

In case a heavy hydrocarbon fraction substantially boiling above 250° C. is recycled from step (ii) to step (i), it may be advantageous to recycle a heavy fraction with a similar or higher boiling range obtained from step (iv) only to the hydrocracking zone of step (iv) and not to step (i), in order to produce additional gasoline. In this case the hydrocracking step is preferably carried out at relatively severe operating conditions such as a temperature of 300°-450° C., a pressure from 30-100 bar, a space velocity from 0.2-2 kg hydrocarbon feed/kg catalyst.hour and a hydrogen/hydrocarbon feed ratio from 1.0-2.0 $Nm^3/kg$.

With the process according to the present invention it is furthermore possible to maximize middle distillate production by recycling gasoline obtained from step (ii), and optionally from step (iv), to step (i) and recycling a hydrocarbon fraction having a boiling range higher than that of middle distillates (i.e., above 350° C.) from step (iv) to at least one of steps (i) and (iv).

The invention furthermore relates to liquid hydrocarbons whenever prepared as described hereinbefore.

The invention is illustrated by the following Examples.

EXAMPLE 1

The effect of the presence of recycled liquid hydrocarbons in oligomerization step (i) of the process according to the invention on the conversion of butene and selectivity for the production of middle distillates (having a boiling range from 150°-350° C.) is illustrated by the following Experiments.

In Comparative Experiment 1 a catalyst A was employed which was prepared by ion exchange of mordenite in the ammonium form at a temperature of 100° C. with an aqueous solution containing one mol nickel-(II) acetate/liter. The resulting catalyst had a molar ratio of nickel:aluminium one after drying at a temperature of 120° C. and calcination in air at a temperature of 500° C. for one hour, and was crushed and sieved to obtain a fraction containing particles having a diameter from 0.18-0.59 mm.

A gas feed mixture containing 40% by weight (w.) of butenes and 60% w. of butanes was passed at a space velocity of 1 kg butenes/kg catalyst.hour through a microflow reactor containing catalyst A at a temperature of 216° C. and a pressure of 16 bar.

In Experiment 2 a gas feed mixture containing 50% w. of butenes and 50% w. of butanes was passed under similar conditions together with normal cetane for which the space velocity was 1 kg n-cetane/kg catalyst.hour over a similar catalyst as used in Experiment No. 1.

The results of Experiments No. 1 and 2 are given in the following Table.

TABLE

| Exp. No. | Time (h) | Conversion (%) | Selectivity (% w) |
| --- | --- | --- | --- |
| 1 | 80 | 85 | 49 |
| 2 | 80 | 94 | 58 |
| 1 | 200 | 75 | 40 |
| 2 | 200 | 90 | 54 |

From the results of the Experiments it is clear that in Experiment No. 2 according to the invention the conversion of butenes and the selectivity towards the production of middle distillates is much higher and more stable after an extended period of time than in Comparative Experiment No. 1 (not according to the invention).

EXAMPLE 2

The effect of recycling gasoline (having a boiling range from 50°-150° C.) in oligomerization step (i) of the present process is illustrated by Experiment No. 3 in which a similar gas feed mixture and catalyst A are employed as in Experiment No. 1. The feed mixture is passed at a temperature of 215° C., a total pressure of 31 bar and a space velocity of 1.0 kg butenes/kg catalyst.hour together with 0.31 kg gasoline/kg catalyst.hour through the microflow reactor.

The resulting conversion of butenes is 98.8% whereas the kerosine selectivity (defined as weight of product fraction boiling from 150°-250° C. divided by weight of product fraction boiling above 150° C., expressed in %) is 59.3.

What is claimed is:

1. Process for preparing liquid hydrocarbons which comprises at least the following steps:
   contacting an olefins-containing feed at oligomerization conditions with a solid oligomerization catalyst comprising nickel on a crystalline aluminum silicate carrier having the structure of a mordenite,
   (ii) separating effluent from step (i) into at least two fractions of which at least one has a boiling range above that of the feed olefins,
   (iii) recycling at least part of a higher boiling fraction obtained from step (ii) to step (i), and
   (v) contacting at least part of a fraction from step (ii) having a boiling range above that of the feed olefins with a hydrocracking catalyst under hydrocracking conditions to produce a reaction effluent.

2. Process according to claim 1 wherein step (iii) a hydrocarbon fraction substantially boiling above 50° C. is recycled to step (i).

3. Process according to claim 2 wherein a hydrocarbon fraction boiling in the gasoline range is recycled to step (i).

4. Process according to claim 1 wherein step (iii) a hydrocarbon fraction boiling from 50° C. up to 220° C., is recycled to step (i).

5. Process according to claim 1 wherein at least part of said reaction effluent obtained from step (iv) is separated into at least two fractions of which at least one has a boiling range of 150° C. and higher.

6. Process according to claim 5 wherein at least part of a hydrocarbon fraction having a boiling range of 150° C. and higher is recycled to at least one of steps (i) and (iv).

* * * * *